United States Patent [19]

Nakaoka

[11] Patent Number: 4,507,610
[45] Date of Patent: Mar. 26, 1985

[54] APPARATUS FOR ELECTROMAGNETICALLY DETECTING FLAWS IN METALLIC OBJECTS

[75] Inventor: Eiichi Nakaoka, Kyoto, Japan

[73] Assignee: Shimadzu Corporation, Kyoto, Japan

[21] Appl. No.: 399,301

[22] Filed: Jul. 19, 1982

[30] Foreign Application Priority Data

Jul. 30, 1981 [JP] Japan .................................. 56-120553
Jul. 30, 1981 [JP] Japan .................................. 56-120554

[51] Int. Cl.³ ...................... G01N 27/82; G01R 33/12
[52] U.S. Cl. .................................. 324/238; 324/233; 324/237; 324/240
[58] Field of Search ................ 324/228, 232, 233–243, 324/226, 329, 262, 219, 220

[56] References Cited

U.S. PATENT DOCUMENTS

| | | | |
|---|---|---|---|
| 2,467,306 | 4/1949 | Habig | 324/242 |
| 3,361,960 | 1/1968 | Renken et al. | 324/241 |
| 3,694,735 | 9/1972 | Mester | 324/260 |
| 3,723,860 | 3/1973 | Loulya et al. | 324/260 X |
| 3,872,379 | 3/1975 | Brooks et al. | 324/224 X |
| 4,286,216 | 8/1981 | Auld et al. | 324/237 |

Primary Examiner—Gerard R. Strecker
Assistant Examiner—Warren S. Edmonds
Attorney, Agent, or Firm—Fidelman, Wolffe & Waldron

[57] ABSTRACT

Nondestructive method of electromagnetically detecting flaws in a metallic object, comprising: placing an object to be tested for flaws adjacent a sensing head which comprises a portion of a sensor ring made of electrically conductive material and arranged inside an electromagnetic coupling coil excited by a high frequency current; causing the object and the sensing head to move relative to each other so that a flaw in the object causes the impedance of the coil to change; and detecting the change of the impedance.

An apparatus for carrying out the method is also provided.

7 Claims, 15 Drawing Figures

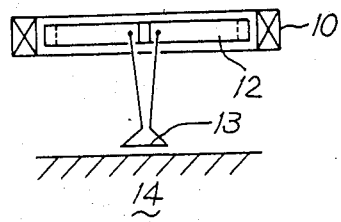
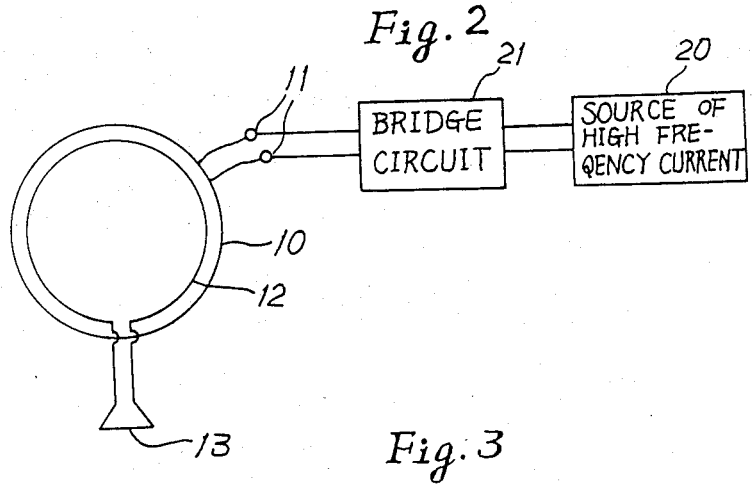
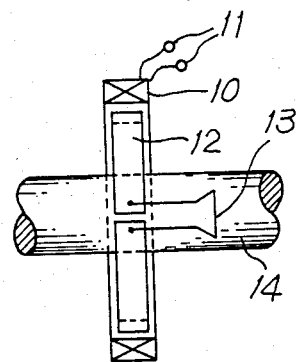

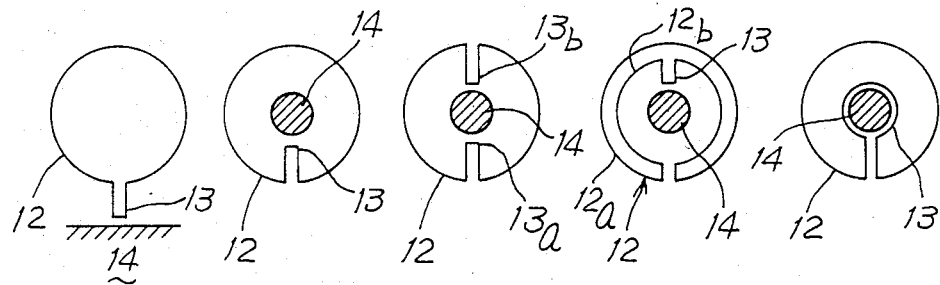
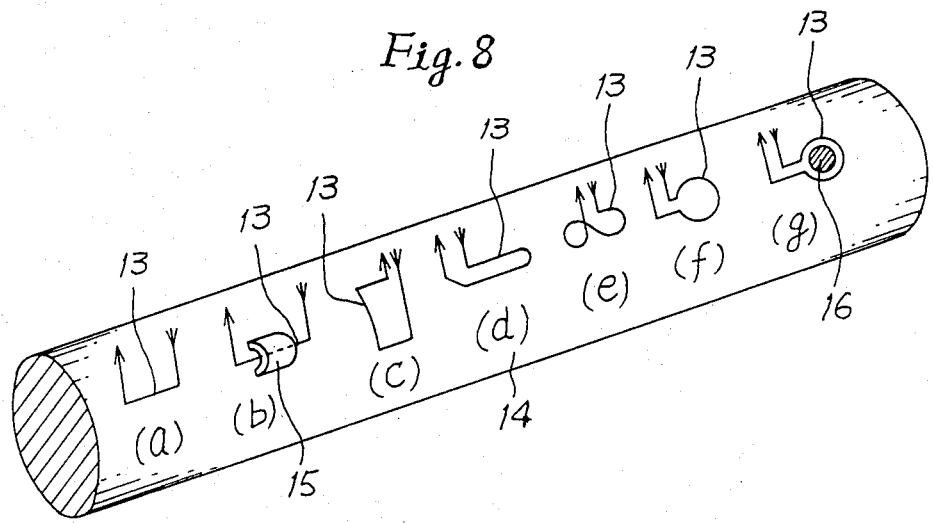

APPARATUS FOR ELECTROMAGNETICALLY DETECTING FLAWS IN METALLIC OBJECTS

BACKGROUND OF THE INVENTION

This invention relates to a nondestructive method and apparatus for electromagnetically detecting defects or flaws in metallic objects.

The nondestructive flaw detecting method which utilizes the principle of electromagnetic induction has been widely used for detection of flaws in various kinds of metallic material since the method enables not only quick and accurate detction of flaws but also recognition of the magnitude of the flaws detected. On the other hand, there has been an increasing demand for improvement of the flaw detecting ability of the apparatus, that is, for quicker and more accurate and stable detection of flaws. For improvement of the flaw detecting ability of the apparatus it is required that the probe or sensor should be made as small as possible and arranged as near as possible to the object being tested and in such a manner as to enable quick scanning of the surface of the object.

If the requirements are to be met, however, the stability of the flaw detecting ablity of the apparatus will have to be more or less sacrificed. Therefore, for stability the detecting ability must be kept at a relatively low level, or alternatively a plurality of sensors are provided so that the whole apparatus becomes large-sized with a resulting increase in the cost for installation.

In an effort to overcome the difficulties the present inventor proposed in Japanese unexamined Patent Publication Nos. 53-135378 and 53-135379 both filed, Apr. 30, 1978, non-destructive methods and devices for electromagnetically detecting flaws in objects, in which a sensor in the form of a magnetic core is rotated within a detecting coil. The methods and devices have substantially broadened the area of detection without reducing the sensitivity of detection. However, the clearance or gap (commonly referred to as the lift-off) between the tip end of the rotary core and the surface of the object being scanned is very small and a wider clearance or lift-off is preferred for easier maintenance.

Accordingly, the primary object of the invention is to provide a nondestructive method of electromagnetically detecting flaws in metallic objects, which is simple, has a high sensitivity with a greater lift-off and is capable of covering a large area at one time and detecting flaws extending in all directions.

Another object of the invention is to provide an apparatus suitable for carrying out the above-mentioned method.

SUMMARY OF THE INVENTION

The invention provides a nondestructive electromanetic flaw detecting method which comprises placing an object to be tested for flaws adjacent a sensing head which comprises a portion of a sensor ring made of electrically conductive material and arranged inside an electromagnetic coupling coil excited by a high frequency current, causing the object and the sensing head to move relative to each other so that a flaw in the object causes the impedance of the coil to change, and detecting the change of the impedance.

The invention also provides a nondestructive electromagnetic flaw detecting apparatus which comprises an electromagnetic coupling coil excited by a high frequency current, a sensor ring made of electrical conductor and arranged inside the coil, with a portion of the conductor being formed into a sensing head, means for supporting an object to be tested for flaws adjacent the sensing head, means for causing relative movement of the sensing head and the object, and means for detecting a change in the impedance of the coil caused by a flaw in the object.

The invention will be described in detail with reference to the drawings.

BRIEF DESCRIPTION OF THE DRAWINGS

FIG. 1 schematically shows the principle of the method of the invention;

FIG. 2 is a top plan view of FIG. 1;

FIG. 3 is a schematic elevational view similar to FIG. 1 but showing a rod-like object being tested;

FIGS. 7a through 7e show different forms of the sensor;

FIGS. 8a through 8e show different forms of the sensing head;

DESCRIPTION OF PREFERRED EMBODIMENTS

Figure 4:
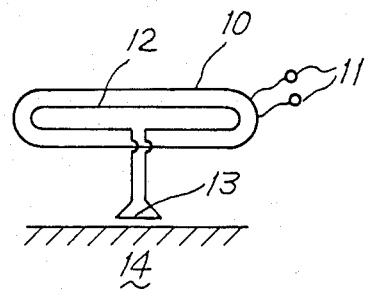
FIG. 4 is a schematic elevational view similar to FIG. 1 but showing another embodiment of the invention.

Referring now to the drawings, first to FIGS. 1 and 2, there is schematically shown an electromagnetic coupling coil 10 comprising a plurality of turns, though shown as a single turn in FIG. 2, with a pair of terminals 11. A split ring 12 of electrically conductive material is disposed inside the coil 10 concentrically therewith. The ring 12 will be referred to as the sensor ring. An electrical conductor 13 to be referred to as the sensing head or probe is connected to the sensor ring 12 to form a closed circuit. The sensing head 13 extends out of the coil 10 so as to be able to be positioned adjacent the surface of an object 14 to be tested for defects or flaws as will be described later in detail. In the present specification the term "sensor" is used to refer collectively to the sensor ring 12 together with the sensing head 13.

The shape of the electromagnetic coupling coil 10 may be not only circular as shown in FIG. 1 but also generally ellipsoidal as shown in FIG. 4. The ellipsodal shape helps reduce the inductance of the coil and induce a large current in the sensor ring 12 and consequently in the sensing head 13.

Figure 5:
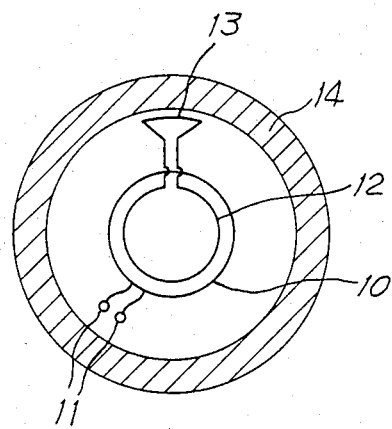
FIG. 5 schematically shows a manner in which the inner surface of a pipe is tested.
Figure 6:
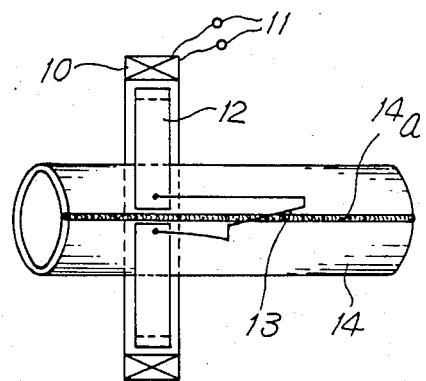
FIG. 6 schematically shows a manner in which a seamed pipe is tested.

The object 14 to be tested can be a flat plate as shown in FIG. 1 or 4, or a rod or bar as shown in FIG. 3, or a pipe as shown in FIG. 5 or 6. The rod or pipe may be circular as shown or of any other shape in cross section.

The object 14 to be tested may be placed outside the sensor ring 10 as shown in FIGS. 1 and 4 no matter whether the object 14 may be a flat plate or a rod or a pipe of any cross-sectional shape. In the latter two cases, the rod or pipe is rotated and simultaneously moved axially, or the rod or pipe is rotated while the sensor is moved alongside the pipe or rod, so that the sensing head traces a spiral line on the outer circumferential surface of the rod or pipe thereby to scan substantially the whole outer circumferential surface of the object being tested.

If the object 14 to be tested is a rod-like member, it may be placed for test inside the sensor ring coaxially therewith so that the rod extends through the ring as shown in FIG. 3. For examination, the sensor may be rotated about the rod while the rod is simultaneously moved axially through the sensor ring 12 so that the sensing head 13 traces a spiral line on the outer circumferential surface of the rod. Also, the rod may be moved axially through the sensor ring 12 so that the sensing head 13 axially and linearly scans the outer surface of the rod from one to the other end of the length of the rod. At the end of one linear scanning stroke, the rod may be rotated for a certain angle, so that as the rod is axially moved again, the sensing head 13 scans a strip of area longitudinally of the rod alongside the linear area it scanned in the previous stroke.

In FIG. 5 the sensor is disposed within the pipe 14 for inspection of the inner circumferential surface of the pipe. As the sensor is rotated about the axis of the pipe 14, it scans the inner circumferential surface of the pipe. Advantageously the sensing head 13 is made linear and lies longitudinally of the pipe for efficient detection of axial flaws on the inner surface of the pipe. If the pipe is axially moved simultaneously with rotation of the sensor, the inner surface of the pipe is spirally scanned by the sensing head.

In FIG. 6 the object 14 is a seamed pipe, the seam of which is to be tested from outside the pipe extending axially through the sensor ring 12. The size, shape and direction of the sensing head 13 must be specifically designed so as to enable efficient detection of flaws in the particular application.

FIGS. 7a through 7e show by way of examples different arrangements of the sensor relative to the object 14 to be tested.

In FIG. 7a sensing head 13 extends or projects out of the sensor ring 12 so as to be disposed adjacent the flat surface of an object 14 to be examined.

In FIG. 7b the sensing head 13 extends radially inwardly of the ring 12 so as to be disposed adjacent the surface of a rod-like object 14 to be tested extending axially through the ring 12.

In FIG. 7c the sensor ring 12 is provided with a diametrically opposed pair of sensing heads 13a and 13b extending radially inwardly of the sensor ring 12 so as to be disposed adjacent the diametrically opposite positions of a rod-like object 14 to be tested extending axially through the ring 12. The provision of two sensing heads increases the efficiency of flaw detection.

In FIG. 7d the sensor ring 12 comprises a pair of two split rings 12a and 12b concentrically arranged one inside the other and electrically connected in series with each other, with the sensing head 13 extending from the inner ring 12b radially inwardly thereof so as to be disposed adjacent an object 14 to be tested. The double-ring arrangement reduces the inductance of the sensor thereby to increase the efficiency of current conversion with the electromagnetic coupling coil not shown in the figure.

In FIG. 7e, the sensing head 13 encircles the outer circumferential surface of an object 14 to be tested extending axially through the sensor ring 12 in a manner similar to the conventional eddy current induction flaw detecting method.

FIGS. 8a through 8e show by way of example different shapes of the sensing head 13.

In FIG. 8a the sensing head 13 extends linearly and longitudinally of the object to be tested. By rotating the object about its axis it is possible to detect flaws extending in the axial direction of the object.

In FIG. 8b the sensing head 13 extends longitudinally of the object to be tested and is provided with a half pipe 15 of a ferromagnetic material such as ferrite to improve the magnetic coupling between the sensing head 13 and the object 14 under test.

In FIG. 8c the sensing head 13 extends linearly circumferentially of the object to be tested and is useful in detecting flaws extending in the circumferential direction as the object is fed in the axial direction.

In FIG. 8d the sensing head 13 comprises a single loop or turn elongated longitudinally of the object to be tested. The arrangement is useful in detecting flaws extending in the axial direction of the object as in the arrangements of FIGS. 8a and 8b.

In FIG. 8e the sensing head 13 is shaped like the figure "8" lying on one side thereof, that is, extending in the axial direction of the rod-like object 14 to be tested. The sensing head may be so arranged that the figure 8 extends circumferentially of the object 14.

In FIG. 8f the sensing head 13 comprises a single circular loop or turn. With this arrangement, the direcion in which flaws lie does not affect the detecting ability of the sensor.

In FIG. 8g the sensing head comprises a single circular loop or turn, with a magnetic core 16 such as a ferrite core arranged within the loop, thereby to improve the electromagnetic coupling between the sensing head and the object under inspection.

The operation of the above-mentioned arrangements will now be described. Since the principles of operation are the same in all of the different arrangements, explanation will be given with reference to FIG. 2. When the electromagnetic coupling coil 10 is supplied with a high frequency current from a source 20 through the terminals 11, the coil 10 produces a high frequency magnetic field, which closely links with the sensor ring 12. Since the ring 12 forms a circuit closed or almost short-circuited by the sensing head 13, a large amount of high frequency current is induced in the sensor ring 12 and flows through the sensing head 13 so that a high frequency magnetic field is produced. The magnetic field excites the object 14 so that a high frequency current is induced locally in the area of the object being tested immediately below the sensing head 13.

Under the condition, if the sensing head 13 and the object 14 under test are moved relative to each other so that any defect or flaw in the object comes to be positioned immediately below the sensing head, the distribution and amount of the high frequency current induced in the area of the object covered by the sensing head change so as to be different from when there was no flaw detected by the sensing head. In other words, the electromagnetic coupling between the sensing head 13 and the object 14 being tested changes with a resulting minute change in the amount and phase of the high frequency current flowing through the sensor ring 12. This means that the impedance as viewed from the terminals 11 of the electromagnetic coupling coil 10 and consequently the high frequency current flowing through the coil has changed. By detecting this change by means of a bridge circuit 21 including the coil 10, it is possible to detect the flaw in the form of an electrical signal.

For scanning the surface of the object 14 to be tested, either or both of the sensing head 13 and the object 14 must be moved relative to the other or each other.

Figure 9:
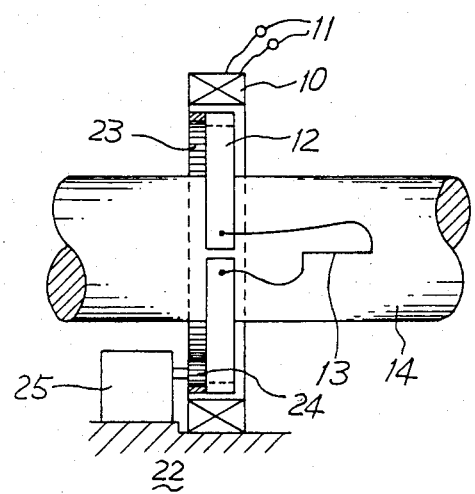
FIG. 9 is a schematic elevational view similar to FIG. 3 with means for rotating the sensor.

FIG. 9 somewhat schematically shows a mechanism for rotating the sensor ring 12 together with the sensing head 13 about a common axis inside the concentric electromagnetic coupling coil 10. The coil 10 is fixed to and supported by a machine frame 22 so that the axis of the coil 10 extends horizontally. An internal ring gear 23 is fixed to the sensor ring 12 for simultaneous rotation. A pinion gear 24 meshes with the internal ring gear 23 so that as the pinion 24 is rotated by a motor 25, the internal ring gear and consequently the sensor ring 12 with the sensing head 13 are rotated about the common axis. If, simultaneously with the rotation of the sensor ring 12, the rod 14 to be tested is axially moved relative to the coil 10 or the sensor ring 12, the sensing head 13 spirally scans the outer circumferential surface of the object. By selecting the feed rate of the object 14 to be tested relative to the rotational speed of the sensing head 13 it is possible to scan substantially the whole outer surface of the object.

Figure 10:
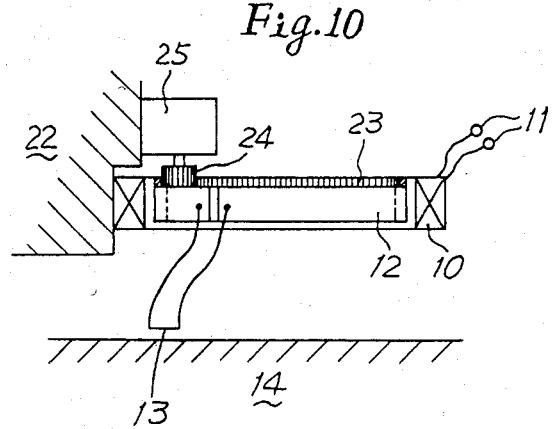
FIG. 10 is a schematic elevational view similar to FIG. 1 with means for rotating the sensor.

FIG. 10 shows a mechanism similar to that of FIG. 9. In FIG. 10 the same reference numerals as in FIG. 9 designate corresponding parts or elements so that no explanation will be given except that the sensing head 13 is arranged outside the sensor ring 12 as in FIG. 1 and adapted to scan the flat surface of an object 14. In FIGS. 9 and 10 the ring 12 is rotatably supported within the coil 10 by suitable means not shown.

Figure 11:
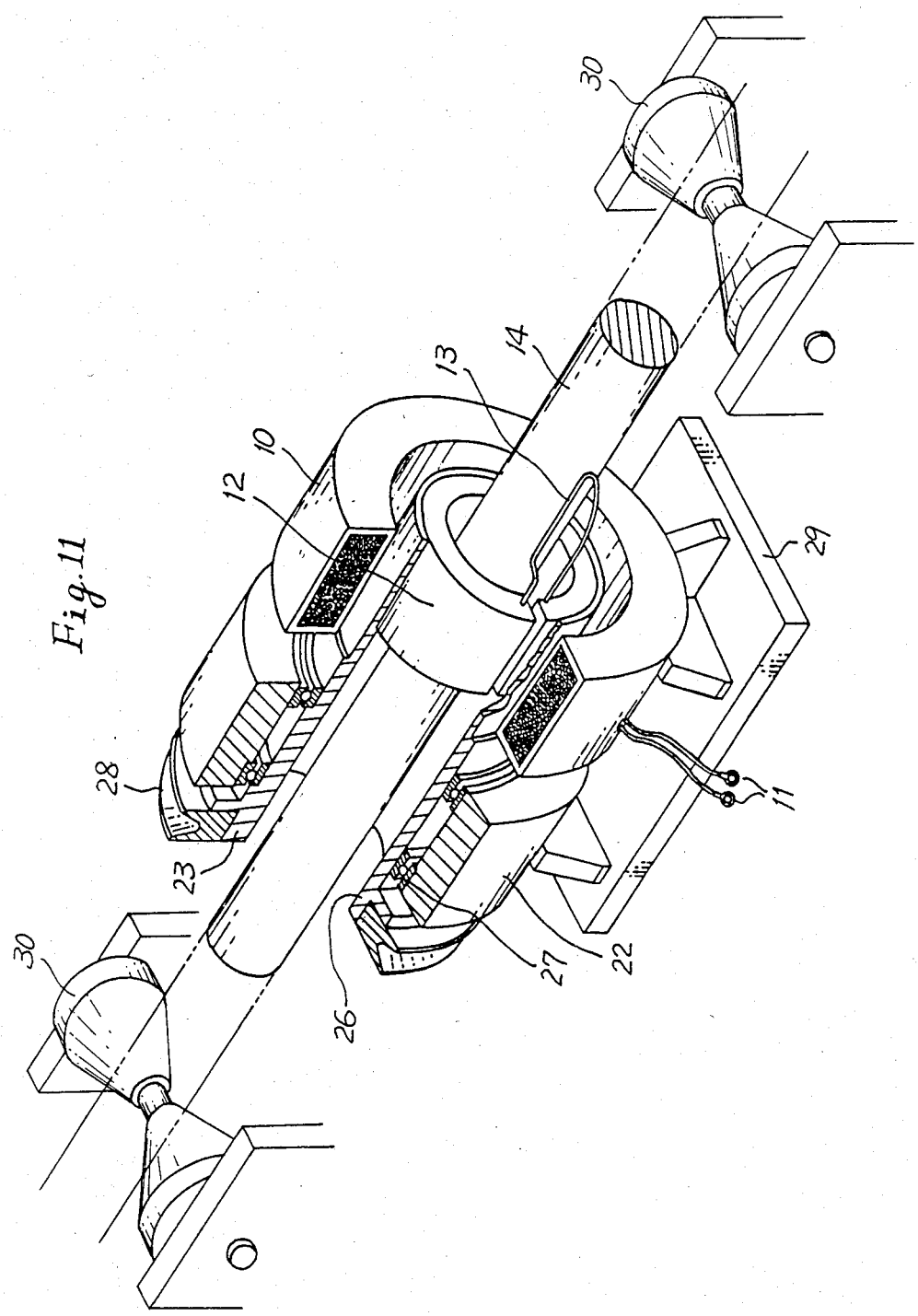
FIG. 11 is a perspective view, partly in section, of a concrete flaw detecting machine constructed in accordance with the invention.

FIG. 11 shows the arrangement of FIG. 9 in a practical form. In FIG. 11, too, the same reference numerals as in FIG. 9 designate corresponding parts or elements. The fixed frame 22 is shown as an annular member which supports a rotatable hollow cylinder 26 through radial ball bearings 27. The sensor ring 12 is fixed to the rotatable hollow cylinder 26 at one end thereof for simultaneous rotation therewith, while a pulley 28 is fixed to the cylinder 26 at the opposite end thereof. A motor not shown drives the pulley 28 through a belt not shown, so that the hollow cylinder 26 and the sensor ring 12 with the sensing head 13 are rotated about the rod-like object 14 to be tested. A base 29 supports the frame 22 and the coil 10. A pair of V-shaped rollers 30 support the object 14 coaxially with the sensor ring 12 so that the object 14 may be moved axially relative to the sensor.

As is apparent from the above description, in accordance with the invention it is only the sensing head 13 that must be placed adjacent the object 14 to be tested for flaws or defects. The shape of the sensing head 13 and the arrangement thereof relative to the object to be tested vary in different applications.

In the illustrated embodiments the sensor ring 12 is provided with one or two sensing heads. The sensor ring may be provided with three or more sensing heads of the same type, if necessary. In order to enable detection of flaws of different types in an object under test at the same time, the sensor ring may also be provided with two or more sensing heads of different types.

Since a high frequency magnetic field is applied to the object under test to induce a high frequency current therein, the object may be of either magnetic or non-magnetic material.

The method of the invention enables detection of flaws in a metallic object not only while the material is cold but also while it is hot.

For relative movement of the sensor and the object to be tested, practically the object is moved. It is possible to move the sensor or both the sensor and the object to be tested. It is also possible to arrange so that while an object to be tested is moved linearly relative to the stationary sensor ring, the sensing head is reciprocated perpendicularly to the direction of the linear movement of the object, or that while a rod-like object to be tested is rotated about its axis, the sensing head is reciprocated perpendicularly to the direction of the linear movement of the object. The arrangement enables zig-zag scanning of the surface of the object thereby to broaden the scanning area.

In accordance with the invention, since the sensing head 13 is taken out of the sensor ring 12 disposed inside the electromagnetic coupling coil 10 and placed adjacent the surface of an object to be tested, the structure of the sensing head is very much simplified and can be applied to objects to be tested having various shapes or contours.

By making the sensing head a long linear line it is possible to effectively detect long flaws. With a relatively large lift-off, the sensitivity of detection can be kept at a high level. In practice, with a 3 mm lift-off, a 50 mm sensing head can detect a 0.3 mm deep flaw with $S/N \geqq 3$.

The method and apparatus of the invention can efficiently detect flaws of various shapes extending in various directions in objects of various shapes or contours.

What I claim is:

1. In an apparatus for electromagnetically detecting flaws in metallic objects of the type employing an electromagnetic coupling coil and an electrically conductive sensor including a sensor ring disposed inside said coupling coil, said coupling coil being connected to an external source of a high frequency current through a bridge circuit such that a first high frequency current excites said coupling coil to produce a first high frequency magnetic field, said first high frequency magnetic field inducing a second high frequency current to flow in said sensor ring, said second high frequency current flowing in said sensor ring producing a second high frequency magnetic field which inturn induces a third high frequency current to flow in said object under test, where during relative movement between said sensor ring and said object under test, a flaw in said object under test will cause a change in the distribution and amount of said third high frequency current induced in said object under test as to cause a change in the amplitude and phase of said second high frequency current flowing in said sensor ring resulting in a corresponding change in the impedance of said coupling coil as seen by said external source of high frequency current through said bridge circuit and producing a corresponding change in the amplitude and phase of said first high frequency current flowing in said coupling coil, whereby a signal corresponding to said change in the amplitude and phase of said first high frequency current flowing in said coupling coil is produced in said bridge circuit, the improvement comprising:

a portion of said sensor formed as a sensor head extending outwardly from said sensor ring and positioned adjacently the surface of said object under test such that said third high frequency current is induced to flow locally in an area of said object under test immediately adjacent said sensing head such that a variation in said third high frequency current caused by a flaw in said object under test located in said area immediately adjacent said sensing head is electromagnetically coupled to said sensing head to cause a chane in the amplitude and phase of said second high frequency current flowing in said sensor ring.

2. The apparatus according to claim 1 further comprising means for causing relative movement of said sensing head and said object under test to each other such that said sensing head scans the surface of said object.

3. The apparatus according to claim 1 wherein said sensor ring comprises a split ring of electrically conductive material disposed concentrically inside said coupling coil and said sensing head comprises an electrically conductive wire connected to said split ring so as to form a closed circuit therewith, said wire having projecting from said split ring a portion adapted to be disposed adjacent the surface of said object under test.

4. The apparatus according to claim 3 wherein said wire is linear.

5. The apparatus according to claim 3 wherein said wire is circular.

6. The apparatus according to claim 3 wherein said wire is curved.

7. The apparatus according to claim 3 wherein said wire is provided with a member of ferromagnetic material.

* * * * *